(12) United States Patent
Smith et al.

(10) Patent No.: US 8,357,130 B2
(45) Date of Patent: Jan. 22, 2013

(54) WOUND CARE APPARATUS

(75) Inventors: Joshua David Smith, Nashville, TN (US); David Myron Smith, Burns, TN (US)

(73) Assignees: Joshua David Smith, Nashville, TN (US); David Myron Smith, Burns, TN (US)

( * ) Notice: Subject to any disclaimer, the term of this patent is extended or adjusted under 35 U.S.C. 154(b) by 459 days.

(21) Appl. No.: 12/033,558

(22) Filed: Feb. 19, 2008

(65) Prior Publication Data

US 2008/0140029 A1    Jun. 12, 2008

Related U.S. Application Data

(63) Continuation-in-part of application No. 11/602,653, filed on Nov. 21, 2006, now Pat. No. 7,648,488.

(60) Provisional application No. 60/890,275, filed on Feb. 16, 2007.

(51) Int. Cl.
*A61F 13/00*    (2006.01)

(52) U.S. Cl. ........ 604/305; 604/304; 604/313; 604/315; 604/308; 604/46

(58) Field of Classification Search .................. 604/304, 604/305, 313, 315, 308, 454, 46
See application file for complete search history.

(56) References Cited

U.S. PATENT DOCUMENTS

| | | |
|---|---|---|
| 4,534,356 A | 8/1985 | Papadakis |
| 4,753,758 A | 6/1988 | Miller |
| 4,979,944 A | 12/1990 | Luzsicza |
| 5,009,635 A | 4/1991 | Scarberry |
| 5,084,011 A * | 1/1992 | Grady .............................. 604/24 |
| 5,636,643 A | 6/1997 | Argenta et al. |
| 5,645,051 A * | 7/1997 | Schultz et al. ........... 128/203.15 |
| 5,645,081 A | 7/1997 | Argental et al. |
| 6,071,267 A | 6/2000 | Zamierowski |
| 6,142,982 A | 11/2000 | Hunt et al. |
| 6,221,025 B1 * | 4/2001 | Skoletsky ..................... 600/504 |
| 6,458,109 B1 * | 10/2002 | Henley et al. ................. 604/304 |

(Continued)

FOREIGN PATENT DOCUMENTS

WO    96/33767    10/1996

(Continued)

OTHER PUBLICATIONS

Madalene C.Y. Heng, MB, FRACP, Faced, Topical Hyberbaric Therapy for Problem Skin Wounds, The Journal of Dermatologic Surgery and Oncology, Aug. 1993, 784-792. vol. 19, Elsevier Science Publishing Co., Inc., New York, New York USA.

(Continued)

*Primary Examiner* — Tatyana Zalukaeva
*Assistant Examiner* — Ilya Treyger
(74) *Attorney, Agent, or Firm* — Renner, Otto, Boisselle & Sklar LLP

(57) ABSTRACT

Disclosed is an apparatus for the treatment of a wound on a patient. The apparatus is capable of administering localized negative pressure therapy to the wound using a hospital wall vacuum source and a drain line for removing exudate from the wound. The apparatus may also be capable of administering localized hyperbaric oxygen therapy to the wound using a hospital wall oxygen source and a supply line for supplying oxygen to the wound. The apparatus includes at least one regulator to control the application of negative pressure therapy and hyperbaric oxygen therapy.

12 Claims, 5 Drawing Sheets

U.S. PATENT DOCUMENTS

| | | | |
|---|---|---|---|
| 6,755,807 | B2 | 6/2004 | Risk, Jr. et al. |
| 6,767,334 | B1 | 7/2004 | Randolph |
| 6,800,074 | B2 | 10/2004 | Henley et al. |
| 6,856,821 | B2 | 2/2005 | Johnson |
| 6,979,324 | B2 | 12/2005 | Bybordi et al. |
| 7,022,113 | B2 * | 4/2006 | Lockwood et al. ........... 604/313 |
| 7,276,051 | B1 | 10/2007 | Henley et al. |
| 7,553,306 | B1 | 6/2009 | Hunt et al. |
| 2003/0212357 | A1 | 11/2003 | Pace |

FOREIGN PATENT DOCUMENTS

| | | |
|---|---|---|
| WO | 00/07653 | 2/2000 |
| WO | 03/092620 | 11/2003 |
| WO | 2005/105174 | 11/2005 |

OTHER PUBLICATIONS

Theodor Kaufman, M.D. et al., The Microclimate Chamber: The Effect of Continuous Topical Administration of 96% Oxygen and 75% Relative Humidty on the Healing Rate of Experimental Deep Burns, The Journal of Trauma, Sep. 1983, 806-815, vol. 23, Williams & Wilkins, Baltimore, MD USA.

Frank E. Johnson, M.D., F.A.C.S., "An Improved Technique for Skin Graft Placement Using a Suction Drain," Surgery Gynecology & Obstetrics, Dec. 1984, 585-586, vol. 159, No. 6, St. Louis, MS USA.

Pal Svedman, "Dressing Allowing Continuous Treatment of a Biosurface", IRCS Medical Science: Biomedical Technology; Clinical Medicine; Surgery and Transplantation, Mar. 27, 1979, One page, Department of Plastic Surgery, Malmo General Hospital, Malmo, Sweden.

Diane M. Cooper, PhD. RN. "The Physiology of Wound Healing: An Overview," Chronic Wound Care: A Clinical Source Book for HealthCare Professionals, 1990, Chapter 1 (1-11), Health Management Publications, Inc., King of Prussia, PA USA.

Keith G. Harding, ME, ChB, MRCGP, "Wound Care: Putting Theory Into Clinical Practice," Chronic Wound Care: A Clinical Source Book for HealthCare Professionals, 1990, Chapter 3 (19-30), Health Management Publications, Inc., King of Prussia, PA USA.

TD Turner, OBE, MPharm, FRPharms, FLS, MCPP, "The Development of Wound Management Products," Chronic would.

TD Turner, OBE, MPharm, PRPharms, FLS, MCPP, "The Development of Wound Management Products," Chronic Wound Care: A Clinical Source Book for HealthCare Professionals, 1990, Chapter 4(31-46), Health Management Publications, Inc., King of Prussia, PA USA.

Katherine F. Jeter, EdD, ET, "Managing Draining Wounds and Fistulae: New and Established Methods," Chronic Wound Care: A Clinical Source Book for HealthCare Professionals, 1990, Chapter 27 (240-246), Health Management Publications, Inc. King of Prussia, PA USA.

Linda K. Klein, BSN, MS:, CETN, "Topical Treatment for Chronic Wounds: An Overview," Chronic Wound Care: A Clinical Source Book for HealthCare Professionals, 1990, Chapter 31 (263-265), Health Management Publications, Inc., King of Prussia, PA USA.

Oscar Alvarez, MD, PhD., "Principles of Moist Wound Healing: Indications for Chronic Wounds," Chronic Wound Care: A Clinical Source Book for HealthCare Professionals, 1990, Chapter 33 (282-289), Health Managements, Inc., King of Prussia, PA USA.

George T. Rodeheaver, PhD., "Controversies in Topical Wound Management: Wound Cleansing and Wound Disinfection", Chronic Wound Care: A Clinical Source Book for HealthCare Professionals, 1990, Chapter 33 (282-289), Health Management Publications, Inc., King of Prussia, PA USA.

S. Randolph May, PhD, "An Algorithm for Wound Management With Natural and Synthethic Dressings", Chronic Wound Care: A Clinical Source Book for HealthCare Professionals, 1990, Chapter 36 (301-308), Health Management Publications, Inc., King of Prussia, PA USA.

Cecilia R. Rund, RN, CETN, "Alternative Treatments—Alternative Settings", Chronic Wound Care: A Clinical Source Book for HealthCare Professionals, 1990, Chapter 37 (309-317), Health Management Publications, Inc., King of Prussia, PA USA.

Keith Van Meter, MD, FACEP, "Baromedicine in Chronic Wound Care", Chronic Wound Care: A Clinical Source Book for HealthCare Professionals, 1990, Chapter 42 (391-409), Health Management Publications, Inc., King of Prussia, PA USA.

Greg Skover, PhD, "New Technologies: an Overview", Chronic Wound Care: A Clinical Source Book for HealthCare Professionals, 1990, Chapter 45 (425-430), Health Management Publications, Inc., King of Prussia, PA USA.

* cited by examiner ial Application No. 60/890,275, filed Feb. 16, 2007, the entirety
WOUND CARE APPARATUS

CROSS-REFERENCES TO RELATED APPLICATIONS

This application claims the benefit of U.S. Provisional Application No. 60/890,275, filed Feb. 16, 2007, the entirety of which is incorporated by reference herein. This application is also a continuation-in-part application of application Ser. No. 11/602,653, filed Nov. 21, 2006 now U.S. Pat. No. 7,648,488, the entirety of which is incorporated by reference herein.

BACKGROUND OF THE INVENTION

The present invention relates generally to wound care treatment and systems for treating wounds. More specifically, the present invention relates to a system designed for alternating applications of vacuum and hyperbaric wound treatments to a wound site.

The patient care industry is continually searching to provide better services, reduce costs, and improve the equipment used to provide the best possible care to the patients. One such way to advance patient care is to improve the treatment of chronic and acute wounds and various types of therapies to treat these wounds. One of two types of treatments is often used to treat chronic and acute wounds: negative pressure therapy or hyperbaric oxygen therapy.

Negative pressure therapy is the controlled application of sub-atmospheric pressure to a wound using a therapy unit, such as a vacuum or suction device, to expose a wound to negative pressure to help promote wound healing. The wound is typically covered to facilitate this negative pressure and suction at the wound area. Various types of resilient, open cell foam surface dressings are typically sealed within an adhesive drape to provide the sub-atmospheric pressure at the wound site. The exudates drained from the wound site are normally directed to a canister that stores the fluids and/or infectious material until properly disposed. The negative pressure wound therapy has been typically prescribed for chronic and acute wound types such as diabetic wounds, pressure ulcers, abdominal wounds, trauma wounds, various burns, flaps and grafts. One of the limitations of negative pressure therapy is that it may be less effective on patients with vascular disorders, such as diabetes, particularly because negative pressure therapy creates a hypoxic environment at the wound. Current research indicates that wound healing is impaired when the oxygen level is 30 millimeters of mercury (mmHg) or less.

Hyperbaric oxygen therapy is the controlled application of greater-than-atmospheric pressures of oxygen to a wound. Oxygen is typically required for all new cell growth, and chronic or non-healing wounds tend to exhibit low oxygen tensions, or tend to be ischemic. A wound can become dormant if the amount of wound tissue that is poorly oxygenated reaches a critical mass. In this state, the body may no longer recognize the need to heal that area, which exacerbates the lack of oxygen in that wound and thus substantially prevents healing of the wound by the body. Oxygen therapy is particularly useful for patients with poor circulation. In addition to helping kill bacteria, oxygen applied to an open wound at a hyperbaric level is dissolved into the wound and absorbed by the surface wound tissue. The cells of the wound tissue that absorb the oxygen will begin metabolic activity in response to the increased oxygen tension. Once the oxygen source is removed, the previously active cells request more oxygen from the body. The body responds by beginning to form new blood cells, and thus, starting the healing process.

Typically, hyperbaric oxygen therapy is performed by placing the patient into a hyperbaric chamber that encompasses the full body of the patient or an entire extremity, such as a leg or an arm. Such chambers are problematic due to their lack of portability, the difficulty in sterilization of the chambers between patients, and the potential adverse effects of breathing oxygen at hyperbaric pressure. It would be preferable if the hyperbaric oxygen treatment were localized at the wound rather than applied to the patient's entire body or extremity.

While both negative pressure and hyperbaric oxygen therapies are each believed to be effective when administered as separate wound care treatments, many patients may benefit from a treatment plan incorporating both negative pressure and hyperbaric oxygen therapies. Because existing hyperbaric oxygen treatment is typically performed in a hyperbaric chamber, switching between negative pressure therapy and hyperbaric oxygen therapy is a long process. Before entering a hyperbaric oxygen chamber, a patient would first have to be disconnected from the negative therapy device and the negative pressure therapy dressing—which typically includes packing materials, a drain, tubing, and sealing material—would have to be removed. Then, following hyperbaric oxygen treatment, a new negative pressure dressing would have to be applied. These procedures are wasteful and time-consuming, making it difficult, if not impossible, to alternate between negative pressure therapy and hyperbaric oxygen therapy every few minutes or less.

In current hospital settings, portable vacuum pumps are often rented or purchased for the purpose of performing negative pressure therapy. Theses suction pumps rented for this procedure called negative pressure wound therapy can rent for $70.00 or $80.00 per day per device and have a cumulative effect of driving up our national health care costs by over one billion dollars. In addition, U.S. patent application Ser. No. 11/602,653, filed Nov. 21, 2006, the entirety of which is also incorporated by reference herein, discloses a combination negative pressure therapy and hyperbaric oxygen therapy treatment system.

The present invention relates to an improved systems and methods for healing wounds.

BRIEF SUMMARY OF THE INVENTION

Disclosed is a method for treating a wound. The method comprises applying to the wound a dressing that engages a drain line; connecting the drain line to a pressure regulator connected to a hospital wall vacuum line associated with a hospital line negative pressure; regulating the pressure applied to the wound such that the pressure applied to the wound is greater than the hospital line negative pressure; and administering negative pressure therapy to the wound via the drain line and less than 1 atmosphere.

In addition, the dressing may also engage a supply line and the method may further include the additional step of connecting the supply line to a pressure regulator connected to a hospital wall oxygen line associated with a hospital line oxygen source. The pressure regulator may then facilitate the administration of hyperbaric oxygen therapy to the wound by regulating the pressure applied to the wound such that the absolute pressure applied to the wound is greater than 1 atmosphere.

Further disclosed is a method for administering the negative pressure therapy and the hyperbaric oxygen therapy intermittently. For example, the negative pressure therapy may administered immediately following the administration of hyperbaric oxygen therapy and hyperbaric oxygen therapy may be administered immediately following the administration of negative pressure therapy. The intermittent delivery of alternating therapies may be cyclical.

The negative pressure therapy also may be administered for a first time period and the hyperbaric oxygen therapy is administered for a second time period such that the first time period is approximately two to three times as long as the second time period. For example, negative pressure therapy may be administered for approximately 20 to approximately 180 seconds and hyperbaric oxygen therapy may be administered for approximately 10 to approximately 60 seconds.

Also disclosed is a method for administering negative pressure wound therapy wherein the wound is subject to an absolute pressure of from approximately 60 mmHg to approximately 160 mmHg during the administration of negative pressure therapy.

Further disclosed is a method for administering hyperbaric oxygen therapy wherein the wound is subject to an absolute pressure of greater than 1 atmosphere during the administration of hyperbaric oxygen therapy.

It is therefore a general object of the present invention to provide an improved apparatus for the treatment of wounds that utilizes the readily available vacuum and gas lines in most hospital rooms.

Another object of the present invention is to provide an apparatus that provides both negative pressure therapy and hyperbaric oxygen therapy to a wound site by utilizing the vacuum line and oxygen supply line available in most hospital rooms.

Also disclosed is a hospital bed with a regulator for controlling negative pressure therapy. The hospital bed includes controls for controlling a pressure regulator connected to a hospital wall vacuum line. The pressure regulator causes the pressure applied to the wound to be greater than the hospital line negative pressure such negative pressure therapy is administered to the wound via the drain line at an absolute pressure at the wound of less than 1 atmosphere.

These and further features of the present invention will be apparent with reference to the following description and attached drawings. In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the spirit and terms of the claims appended hereto.

Features that are described and/or illustrated with respect to one embodiment may be used in the same way or in a similar way in one or more other embodiments and/or in combination with or instead of the features of the other embodiments.

DETAILED DESCRIPTION OF THE INVENTION

The invention relates to a novel therapeutic method and apparatus capable of administering negative pressure therapy using the common vacuum wall line available in most hospital rooms. Preferably, the apparatus is also capable of administering hyperbaric oxygen therapy using the oxygen supply line available in almost all hospital rooms. In addition, it is preferable that apparatus be capable of administering the negative pressure therapy and hyperbaric oxygen therapy to the wound area intermittently in order to both remove exudate from the wound and infuse oxygen into the wound. It is believed that the controlled application of these therapies can greatly increase wound-healing success, both clinically and aesthetically, and minimize wound healing time.

The apparatus includes a drain line that attaches to a hospital wall vacuum line and is used to remove exudate from the wound. The drain line may be unique in that it is partially composed of suction tubing and one-way check valves to ensure the delivery of fluid to the collection canister from the wound. The apparatus further includes at least a pressure regulator for controlling the pressure applied to the wound via the drain line during negative pressure therapy. In addition, the apparatus may also include a supply line that attaches to a hospital wall oxygen line or a fluid reservoir. The hospital wall oxygen line is used to supply oxygen to the wound under pressure. The fluid reservoir may also introduce oxygen or other fluid to the system. A regulator is used to control the pressure applied to the wound during the administration of hyperbaric oxygen therapy. The apparatus is preferably capable of alternating between negative pressure therapy and hyperbaric oxygen therapy in an automated manner without requiring clinician assistance and without necessitating a wound dressing change.

Figure 1:
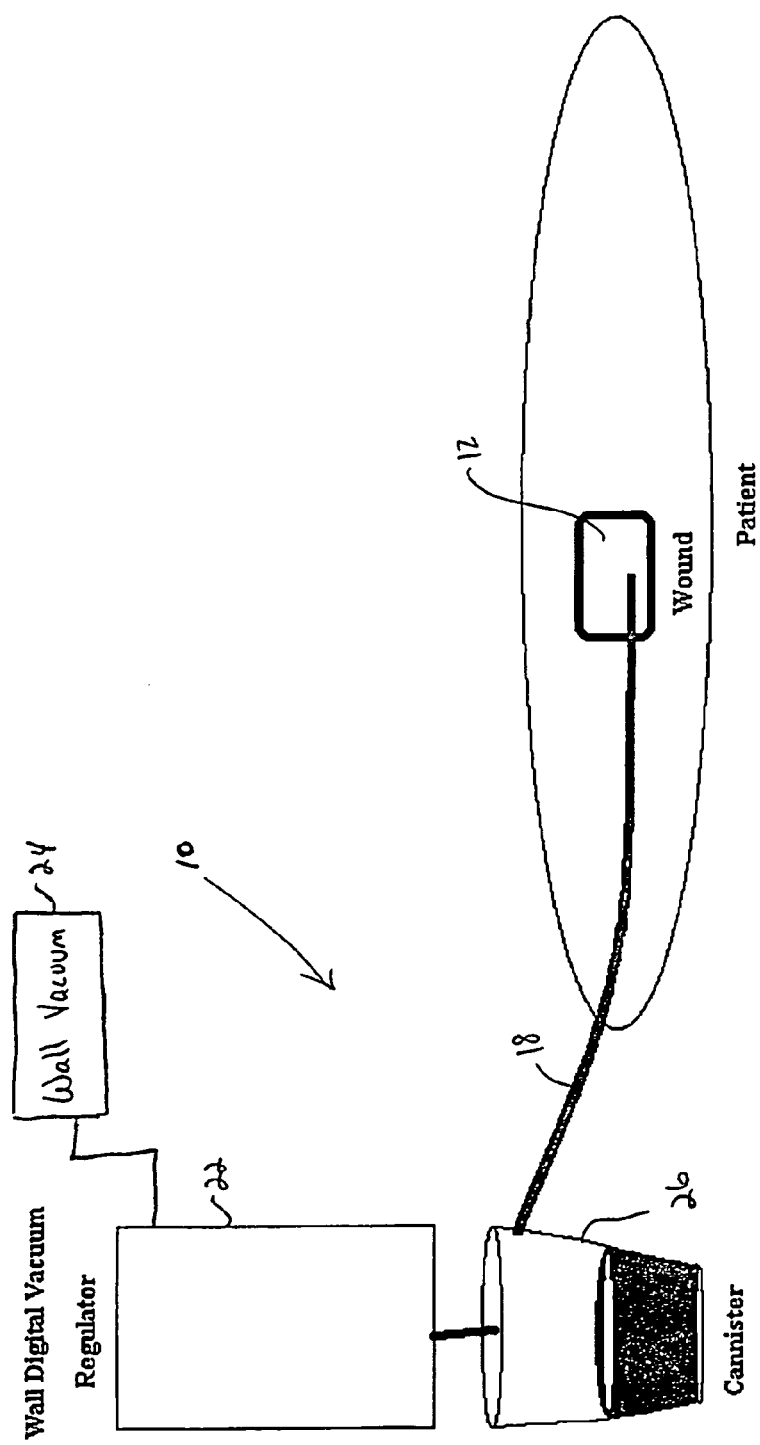
FIG. 1 is a schematic view of a pressure regulating apparatus for regulating negative pressure therapy in accordance with the current disclosure.

Referring generally now to FIG. 1, a wound treatment apparatus 10 according to the present invention is illustrated schematically. The apparatus 10 includes a drain line 18 that is operably engaged with a hospital wall vacuum line 24. The drain line 18 is preferably positioned to remove exudates from the wound 12. A negative pressure regulator 22 functions to control the negative pressure therapy administered by the wound treatment apparatus 10 to the wound 12.

As will be understood by those skilled in the art, the negative pressure regulator 22 is preferably a pressure regulator such as an Amvex Corporation pressure regulator. An example of such a regulator can be found in U.S. Pat. Nos. 7,143,773 and 6,960,190, which are incorporated herein by reference. Preferably, the negative pressure regulator 22 is capable of both intermittent and continuous administration of negative pressure and has a digital control system where pressures are digitally set and maintained. In the presently preferred embodiment, a negative pressure regulator 22 is adapted to attach to a hospital wall vacuum or gas line 24 in a hospital room with a portion being modular for convenient placement and administration of negative pressure.

The negative pressure regulator also preferably comprises safety features that will digitally monitor and limit the application of negative pressure therapy to protect delicate tissues and organs in the event of negative pressure fluctuations between 1-20 mmHg in the vacuum system. Other safety features may include leak alarms, high negative pressure alarms, and convenient mounting hardware. These alerts and alarms may be transmitted wirelessly to the nurses monitoring station or through an alarm cable attaching the NPWT device to the hospital alarm system.

In use, the negative pressure regulator 22 can cause the wound treatment apparatus 10 to administer negative pressure therapy to the wound 12 via the drain line 18. The negative pressure causes exudates to be removed from the wound 12 and to travel to travel through the drain line 18 to a canister 26, which is any suitable container for exudates.

Figure 2:
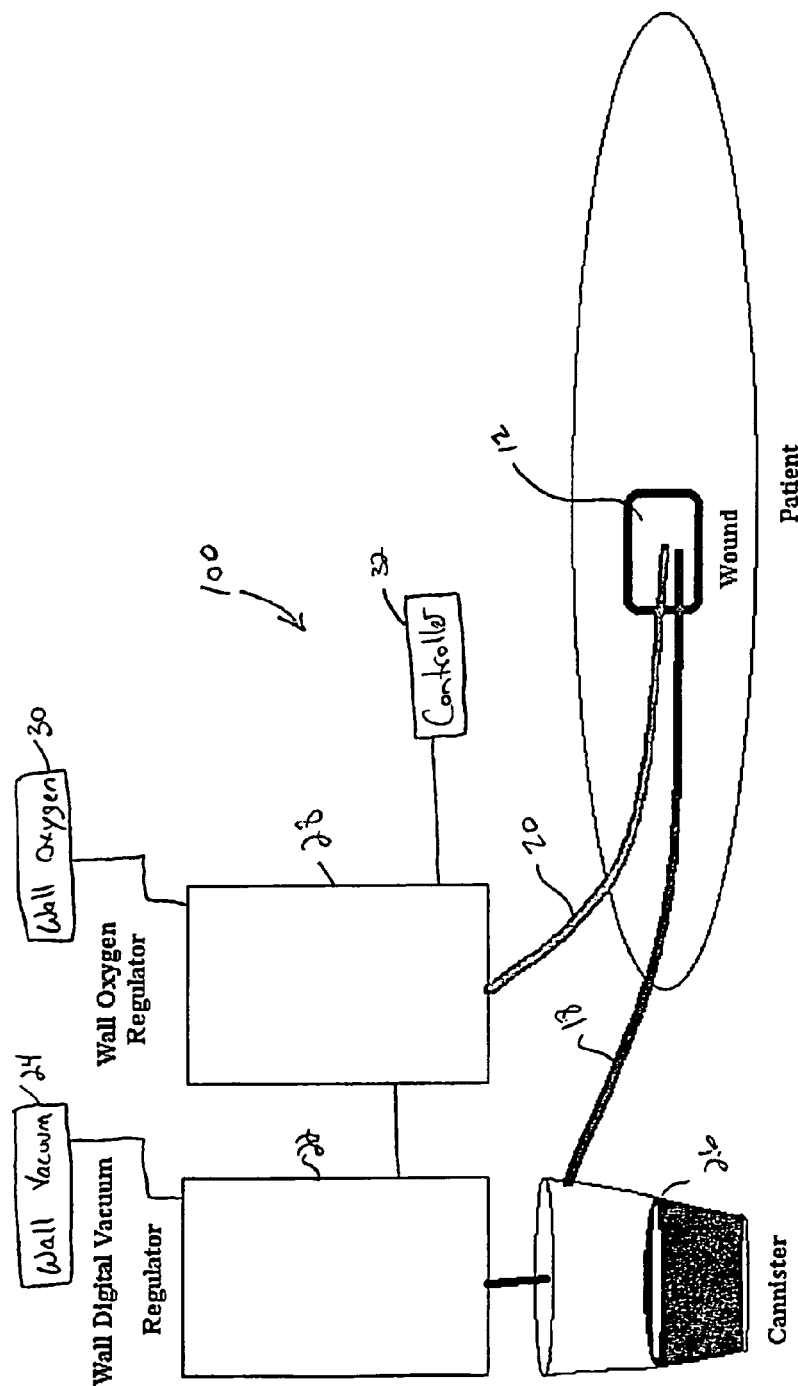
FIG. 2 is a schematic view of a pressure regulating apparatus for regulating negative pressure therapy and hyperbaric oxygen therapy in accordance with the current disclosure.

Turning next to FIG. 2, is a schematic view of a pressure regulating apparatus for regulating negative pressure therapy and hyperbaric oxygen therapy is disclosed. Like the apparatus 10 of FIG. 1, the apparatus 100 includes a drain line 18 that is operably engaged with a hospital wall vacuum line 14. The drain line 18 is preferably positioned to remove exudates from the wound 12. A negative pressure regulator 22 functions to control the therapy administered by the wound treatment apparatus 10 to the wound 12 by causing the wound treatment apparatus 100 to administer negative pressure therapy to the wound 12 via the drain line 18. The negative pressure causes exudates to be removed from the wound 12 and to travel to travel through the drain line 18 to a canister 26, which is any suitable container for exudates.

In addition, the apparatus 100 of FIG. 2 also includes a supply line 20 that is operably engaged with a hospital wall oxygen line 30 and positioned to supply oxygen to the wound 12. An oxygen regulator 28 functions to control the hyperbaric oxygen therapy administered by the wound treatment apparatus 10 to the wound 12. In use, hyperbaric oxygen regulator 28 can cause the wound treatment apparatus 10 to administer hyperbaric oxygen therapy to the wound 12 via the supply line 20.

It will be understood by those skilled in the art the negative pressure regulator 22 and the oxygen regulator 28 may be implemented as a single regulator and that the single regulator may be configured to function intermittently.

In operation, negative pressure therapy and hyperbaric oxygen therapy may each be administered intermittently. In other words, negative pressure therapy and hyperbaric oxygen therapy may be administered in alternating treatments where the wound treatment apparatus 10 cycles between negative pressure therapy and hyperbaric oxygen therapy or, only one type of treatment (i.e. negative pressure therapy or hyperbaric oxygen therapy) may be administered in an intermittent manner such that the wound treatment apparatus 10 cycles between administering treatment to the wound 12 and not administering treatment to the wound 12.

For example, the apparatus 100 may include a controller 32 that is configured to cause negative pressure therapy to be administered to the wound 12 via the drain line 18 for a first time period and hyperbaric oxygen therapy to be administered to the wound 12 via the supply line 20 for a second time period. In one presently preferred embodiment, the first time period during which negative pressure therapy is administered is approximately two to three times as long as the second time period during which hyperbaric oxygen therapy is administered. The controller 32 may be further configured to cause hyperbaric oxygen therapy to be administered immediately following the cessation of the administration of negative pressure therapy and to cause negative pressure therapy to be administered immediately following the cessation of the administration of hyperbaric oxygen therapy.

The administration of negative pressure therapy and hyperbaric oxygen therapy may be controlled using a variety of methods. For example, the hospital wall oxygen line 16 may be configured to supply a constant flow of fluid. The controller 32 may be configured to cause the administration of negative pressure therapy by activating the hospital wall vacuum line 14, which would create a negative pressure environment at the wound 12 even though the wound 12 would continue to be exposed to fluid from the hospital wall oxygen line 16. The controller 32 may be further configured to cause the administration of hyperbaric oxygen therapy by deactivating the hospital wall vacuum line 14, thereby causing the wound 12 to be exposed only to the fluid from the hospital wall oxygen line 16 and causing pressures at the wound 12 to build to hyperbaric levels determined by, among other factors, the flow rate of the fluid.

Another mechanism for controlling the administration of negative pressure therapy and hyperbaric oxygen therapy is to use the controller 32 to control both the hospital wall vacuum line 14 and the hospital wall oxygen line 16. Thus, the controller 32 may be configured to cause the administration of negative pressure therapy by activating the hospital wall vacuum line 14 and either reducing the flow from or deactivating the hospital wall oxygen line 16. Similarly, the controller 32 may be further configured to cause the administration of hyperbaric oxygen therapy by deactivating the hospital wall vacuum line 14 and increasing the flow of fluid from the hospital wall oxygen line 16.

Alternatively, the controller 32 may include two controllers, one for each device. The controller that controls the hospital wall oxygen line 16 may be configured to detect the state of the hospital wall vacuum line 14 or the state of the environment surrounding the wound 12. Upon determining an end of a negative pressure therapy cycle, the controller controlling the hospital wall oxygen line 16 could cause the administration of hyperbaric oxygen therapy by activating or increasing the fluid flow from the hospital wall oxygen line 16. Conversely, the controller that controls the hospital wall vacuum line 14 could be configured to detect the state of the hospital wall oxygen line 16 or the state of the environment surrounding the wound 12. Upon determining an end of a hyperbaric oxygen therapy cycle, the controller controlling the hospital wall vacuum line 14 could cause the administration of negative pressure therapy by activating the hospital wall vacuum line 14.

While each of the negative pressure therapy and the hyperbaric oxygen therapy could potentially be administered to the wound 12 for hours before alternating to the other therapy, it is presently preferred that the controller 32 cause negative pressure therapy to be administered to the wound 12 for relatively short periods of time. For example, negative pressure therapy may be administered for approximately 20 seconds to approximately 180 seconds before moving on to hyperbaric oxygen therapy or to non-therapy in the event that the apparatus is set to intermittently apply only negative pressure therapy. Similarly, the controller 32 may cause hyperbaric oxygen therapy to be administered to the wound 12 for approximately 10 seconds to approximately 60 seconds before moving on to negative pressure therapy or to non-therapy in the event that the apparatus is set to intermittently apply only hyperbaric pressure therapy.

Moreover, the negative pressure therapy and the hyperbaric oxygen therapy may be administered in a cyclical manner. For each cycle consisting of negative pressure therapy administration and hyperbaric oxygen therapy administration, the administration of hyperbaric oxygen therapy may be limited to no more than 30 minutes. In other words, following the administration of negative pressure therapy for a first time period, hyperbaric oxygen therapy is administered for no more than 30 minutes, after which the negative pressure therapy is administered again for some time period, which may be the same as the first time period. Hyperbaric oxygen therapy would then preferably be administered again for no more than 30 minutes, after which negative pressure therapy would be administered again.

In addition, the controller 32 may also be capable of selectively causing the cessation of negative pressure therapy without causing the cessation of the hyperbaric oxygen therapy. Similarly, the controller 32 is preferably configured to be capable of selectively causing the cessation of hyperbaric oxygen therapy without causing the cessation of the negative pressure therapy.

As will be understood by those of skill in the art, the administration of negative pressure therapy generally involves exposing the wound 12 to pressures of less than 1 atmosphere. The pressures employed during negative pressure therapy may include absolute pressures ranging from approximately 0 mmHg to approximately 300 mmHg. Preferably, the absolute pressure ranges from approximately 60 mmHg to approximately 160 mmHg during the administration of negative pressure therapy.

As will also be understood by those of skill in the art, the administration of hyperbaric oxygen therapy involves exposing the wound 12 to a fluid at greater than atmospheric pressures. Preferably, the wound 12 is subjected to an absolute pressure ranging from approximately 1.5 atmospheres to approximately 3 atmospheres during the administration of hyperbaric oxygen therapy.

The hospital wall vacuum line 14 can be any suitable suction device such as a vacuum, a manual, mechanical, or electrical pump, a hospital room suction line, or any other device exhibiting vacuum or suction capabilities. The hospital wall oxygen line 16 can be a suitable fluid supply device and preferably is an oxygen source or a humidified oxygen source, such as an oxygen concentrator, oxygen canister, or oxygen supplied from a hospital room oxygen line. For example, the hospital wall oxygen line 16 may administer oxygen or humidified oxygen at approximately 0.1 liters per minute to approximately 3 liters per minute. Preferably, the hospital wall oxygen line 16 administers oxygen or humidified oxygen at approximately 1 liter per minute to approximately 2 liters per minute.

Also, the hospital wall vacuum line controller 14 and the hospital wall oxygen line controller 16 may be powered by a single power source, such as a wall plug or a rechargeable battery, and may share a power supply.

The drain line 18 may be surgical tubing, oxygen tubing or any other suitable type of line for removing exudate from a wound site and may have one-way check valves connected within it. The supply line 20 may be surgical tubing, oxygen tubing or any other suitable type of line for carrying fluid, such as oxygen, to a wound site and may be passively engaged by the vacuum source or independently supplied by the fluid source. In addition, part of the drain line 18 and part of the supply line 20 may be formed by a multi-lumen tube.

To perform localized administration of negative pressure therapy and hyperbaric oxygen therapy, the drain line 18 and supply line 20 preferably engage a wound dressing. The dressing includes packing material above the wound 12 and a drain atop the packing material. The packing material may be, for example, gauze, foam dressing/packing, sponges, or the like. Preferably, the packing material is anti-microbial gauze saturated with saline.

The drain device may be included as part of the drain line 18 or attached to the end of the drain line 18 opposite the hospital wall vacuum line 14. Suitable drain devices include Jackson-Pratt silicon drain, flat drain, round channel drain, fluted drain, drain tube, Kremlin drain, or other drains capable of removing exudates from within or on top of the wound 12.

Atop the drain is more packing material. The dressing further has a gasket made from pliable adhesive material molded around the surrounding edge of the wound. The drain line 18 and the supply line 20 are atop the gasket. Optionally, additional gasket material is included atop the drain line 18 and supply line 20 for engaging the drain line 18 and the supply line 20. The gasket material may be, for example, an Eakin Cohesive Seal.

Sealing material surrounds the wound 12, the drain 24, the packing material and the gasket. The sealing material can adhere to the gasket and the skin surrounding the wound 12. Preferably, the dressing is capable of maintaining adherence during administration of hyperbaric oxygen therapy at pressures of at least 3 atmospheres. The sealing material 40 preferably has adhesive properties to withstand the pressure induced by the supply of hyperbaric oxygen from the hospital wall oxygen line 16 and the negative pressures drawn by the hospital wall vacuum line 14.

It will be understood by those skilled in the art that various types of dressings may be used. For example, the drain may be positioned above the packing material or below the packing material, as opposed to sandwiched between packing material as shown. Also, the drain and sealing material may be incorporated as one device. In addition, the dressing may also include a protective mesh separating the packing material from the wound.

Figure 3:
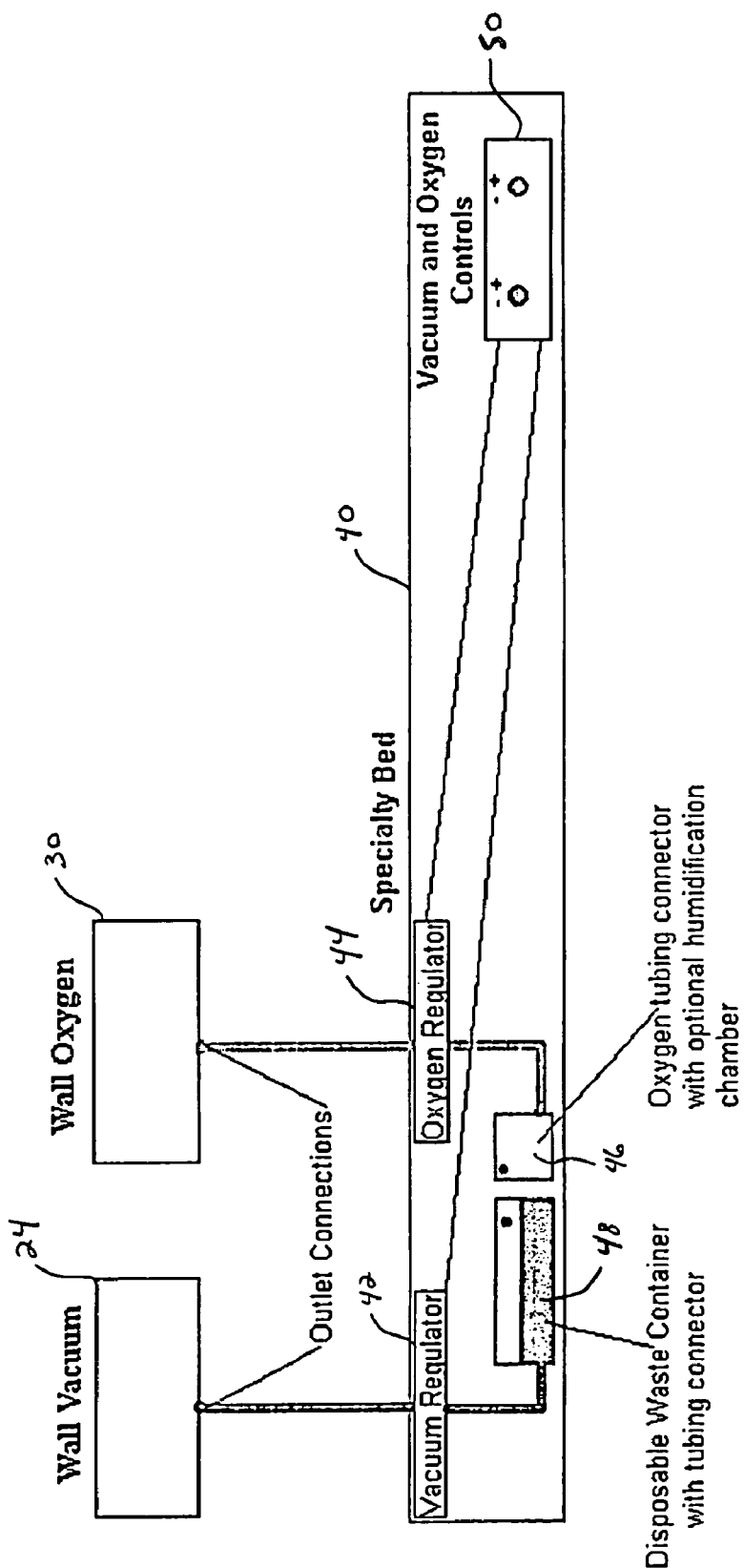
FIG. 3 is a schematic view of a pressure regulating apparatus for regulating negative pressure therapy and hyperbaric oxygen therapy in conjunction with a specialty hospital bed in accordance with the current disclosure.

Turning next to FIG. 3, a schematic illustration of a hospital bed embodiment of apparatus made in accordance with the current disclosure is provided. Because of the presence of both a negative pressure supply 14 and a fluid supply 16 in many hospital rooms, it may be desirable to incorporate the controller into a hospital bed, which may include the bed frame and/or the mattress. Thus, the controller in a hospital bed is preferably used to administer negative pressure therapy and hyperbaric pressure therapy on a wound 12 using a hospital room suction line as the hospital wall vacuum line 14 and the hospital room oxygen line as the hospital wall oxygen line 16. As illustrated in FIG. 3, the hospital bed 40 includes an oxygen regulator 44, a negative pressure regulator 42, a waste canister 48 and an optional humidification chamber 46 operably engaged with the oxygen regulator 44. In addition, the hospital bed 40 preferably includes user controls 50 for making adjustments to the negative pressure therapy and/or hyperbaric oxygen therapy. In use, the hospital bed 40 of FIG. 3 is preferably capable of operating in the same manner as the apparatus 100 of FIG. 2.

In addition, the system can be configured such that the oxygen supply line is passively activated by the application of negative pressure therapy, where the supply line draws in a steady supply of fluid from a reservoir to the system.

Figure 4:
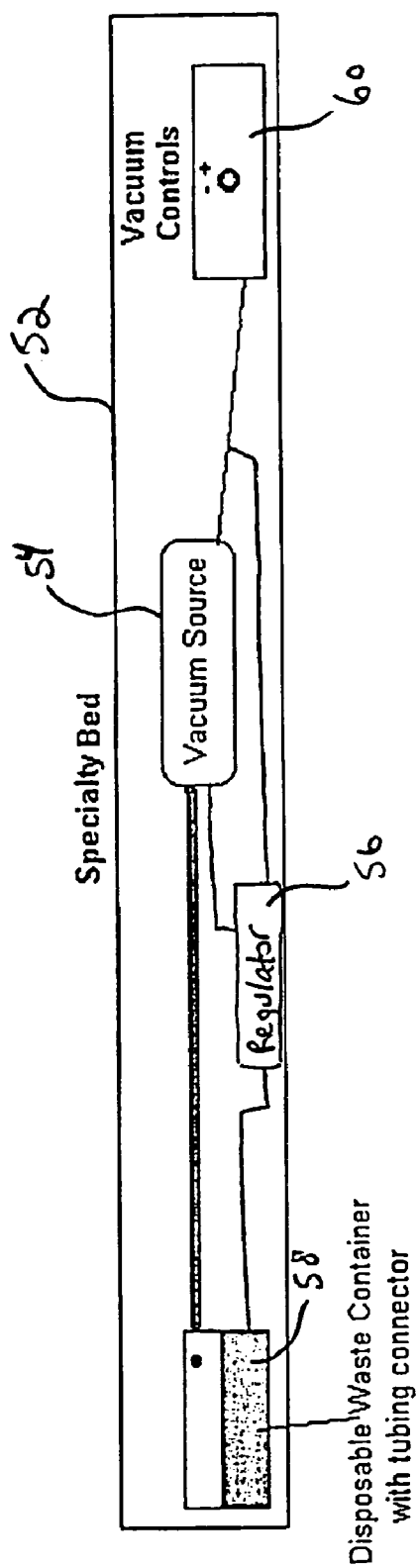
FIG. 4 is a schematic illustration of a specialty negative pressure therapy hospital bed made in accordance with the current disclosure.

Turning next to FIG. 4, another specialty hospital bed is disclosed. The hospital bed 52 of FIG. 4 is preferably capable of operating in the same manner as the apparatus 10 of FIG. 1, except that the negative pressure therapy regulation system is incorporated into a hospital bed 52. The hospital bed includes a local negative pressure source 54, exudates canister 58 and regulator 56. The hospital bed also includes controls 60 for making adjustments to the negative pressure therapy.

Figure 5:
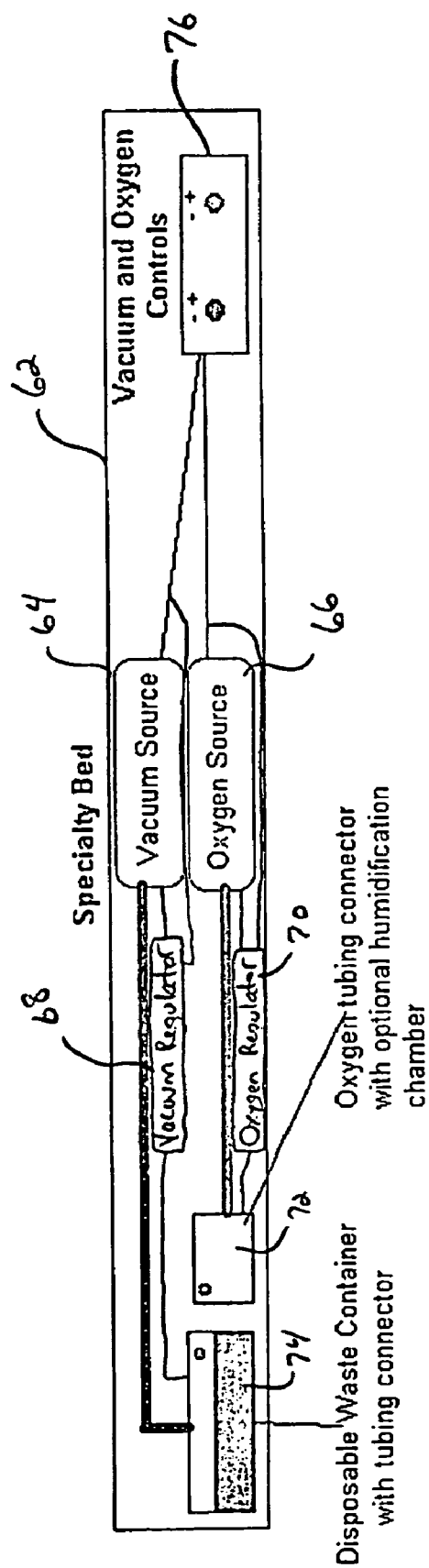
FIG. 5 is a schematic illustration of a specialty negative pressure therapy and hyperbaric oxygen therapy hospital bed made in accordance with the current disclosure.

Turning next to FIG. 5, another specialty hospital bed is disclosed. The hospital bed 62 of FIG. 5 is similar to the hospital bed 40 of FIG. 3 except the hospital bed 62 of FIG. 5 includes a local negative pressure source 64 and a local hyperbaric oxygen source 66. Thus, rather than being configured to interact with a hospital wall vacuum line and a hospital wall oxygen line, the bed of FIG. 5 includes its own vacuum 64 and oxygen source 66. Like FIG. 3, the hospital bed 62 includes an oxygen regulator 60, a negative pressure regulator 68, a waste canister 74 and an optional humidification chamber 72 operably engaged with the oxygen regulator 70. In addition, the hospital bed 62 preferably includes user controls 76 for making adjustments to the negative pressure therapy and/or hyperbaric oxygen therapy.

Although the invention has been shown and described with respect to certain embodiments, it is obvious that equivalents and modifications will occur to others skilled in the art upon the reading and understanding of the specification. The present invention includes all such equivalents and modifications, and is limited only by the scope of the following claims.

What is claimed is:

1. A method for treating a wound comprising:
   connecting the supply line to a pressure regulator connected to a hospital wall oxygen line associated with a hospital line oxygen source
   regulating the pressure applied to the wound via the drain line such that the pressure applied to the wound is greater than the hospital line negative pressure;
   regulating the pressure applied to the wound via the supply line such that the pressure applied to the wound is less than the hospital wall oxygen line pressure;
   administering hyperbaric fluid therapy to the wound via the supply line for approximately 10 seconds to approximately 60 seconds; and
   administering negative pressure therapy to the wound via the drain line at less than 1 atmosphere for approximately 20 seconds to approximately 180 seconds;
   wherein the hyperbaric oxygen therapy and the negative pressure therapy are administered intermittently such that negative pressure therapy is administered immediately following the administration of hyperbaric oxygen therapy and hyperbaric oxygen therapy is administered immediately following the administration of negative pressure therapy.

2. The method of claim 1, wherein the supply line draws in a steady supply of fluid from a reservoir to the system and is passively activated by the application of negative pressure wound therapy.

3. The method of claim 1, wherein the wound is subject to an absolute pressure of from approximately 60 mmHg to approximately 160 mmHg during the administration of negative pressure therapy.

4. The method of claim 1, wherein administering hyperbaric oxygen therapy comprises supplying oxygen to the wound wherein the oxygen comprises at least one of: oxygen or humidified oxygen.

5. The method of claim 4, wherein the oxygen or humidified oxygen is administered at approximately 0.1 liters per minute to approximately 3 liters per minute.

6. The method of claim 1, wherein administering hyperbaric oxygen therapy comprises supplying oxygen to the wound, wherein the oxygen comprises at least one non-oxygen drug.

7. The method of claim 6, wherein the non-oxygen drug is supplied in powder form via gas.

8. The method of claim 7, wherein the non-oxygen drug is supplied in vapor form via humidified gas.

9. The method of claim 8, wherein the non-oxygen drug is supplied via a humidification device operatively connected to the supply line.

10. The method of claim 1, further comprising receiving information from a diffusion sensor relating to the diffusion into the wound of oxygen supplied at least during hyperbaric oxygen therapy.

11. The method of claim 10, further comprising increasing the oxygen flow rate or the pressure at the wound during hyperbaric oxygen therapy in response to information received from the diffusion sensor indicating that the oxygen diffusion rate is below a desired level.

12. The method of claim 10, further comprising increasing the duration of the administration of hyperbaric oxygen therapy relative to the negative pressure therapy in response to information received from the diffusion sensor indicating that the oxygen diffusion rate is below a desired level.

* * * * *